United States Patent [19]
Wong

[11] Patent Number: 5,369,397
[45] Date of Patent: Nov. 29, 1994

[54] ADAPTIVE FIRE DETECTOR
[75] Inventor: Jacob Y. Wong, Santa Barbara, Calif.
[73] Assignee: Gaztech International Corporation, Goleta, Calif.
[21] Appl. No.: 874,394
[22] Filed: Apr. 27, 1992

Related U.S. Application Data

[63] Continuation-in-part of Ser. No. 851,869, Mar. 16, 1992.

[51] Int. Cl.$^5$ ............................................. G08B 17/10
[52] U.S. Cl. .................................... 340/632; 73/31.01
[58] Field of Search ..................... 340/627, 628, 632; 250/573; 73/23.31, 24.02, 31.01

[56] References Cited

U.S. PATENT DOCUMENTS 4,288,790 9/1981 Schnell ............................... 340/628
4,526,028 7/1985 Hübner ........................... 340/632 X
5,053,754 10/1991 Wong ................................. 340/632

Primary Examiner—Jeffery A. Hofsass
Attorney, Agent, or Firm—Daniel C. McKown

[57] ABSTRACT

The fire detector includes a carbon dioxide sensor and a microcomputer. When the rate of increase of the concentration of carbon dioxide at the sensor exceeds a threshold, an alarm is produced. The threshold is set at one of three possible levels by the microcomputer in response to the state of the atmosphere at the sensor as determined by the microcomputer based on several variables that are derived from the sensed concentration of carbon dioxide. The derived variables include the average concentration of carbon dioxide, the average rate of change of carbon dioxide concentration, the monotonicity of the increase or decrease of the carbon dioxide concentration and the range of concentrations sensed in each cycle of operation. The threshold setting is determined every ten seconds. In this way, the setting of the rate threshold is responsive to variations in the carbon dioxide level at the sensor that are caused by entities other than a fire, such as the presence or absence of people in a closed room.

10 Claims, 5 Drawing Sheets

| AVERAGE | | RATE | MONO | RANGE | | STATE |
| --- | --- | --- | --- | --- | --- | --- |
| <800 | >1000 | 1=+<br>0=− | 1=YES<br>0=NO | <5 | >30 | |
| 0 | 1 | 1 | 1 | 0 | 1 | HIGH |
| 0 | 0 | | | | | MEDIAL |
| 1 | 0 | 1 | | | | MEDIAL |
| 1 | 0 | 0 | 0 | | | MEDIAL |
| 1 | 0 | 0 | 1 | 0 | | MEDIAL |
| 0 | 1 | 0 | | 0 | | MEDIAL |
| 1 | 0 | 0 | 1 | 1 | 0 | LOW |
| 0 | 1 | 0 | | 1 | 0 | LOW |
| 0 | 1 | 1 | 0 | 1 | | LOW |
| 0 | 1 | 1 | 1 | 1 | 0 | LOW |

FIG. 5

ADAPTIVE FIRE DETECTOR

REFERENCE TO RELATED APPLICATIONS

This application is a continuation-in-part of U.S. patent application Ser. No. 07/851,869 filed Mar. 16, 1992 for "NDIR Gas Analysis Using Spectral Ratioing Technique" in which a carbon dioxide sensor was described.

BACKGROUND OF THE INVENTION

1. Field of the Invention

The present invention is in the field of fire alarms and more specifically relates to a fire-detecting system that uses a microprocessor for varying the alarm threshold to adapt the fire detector to varying ambient conditions, so as to increase the speed of response of the system and to reduce its false alarm rate.

2. The Prior Art

The related U.S. patent application Ser. No. 07/851,869 describes the structure and operation of a carbon dioxide sensor that produces an output signal representative of the concentration of carbon dioxide in the air immediately surrounding the sensor. In contrast, the emphasis in the present application is on the use made of the output signal for determining when a fire is present. In U.S. Pat. No. 5,053,754 issued Oct. 1, 1991 to the present inventor for "Simple Fire Detector" and in U.S. Pat. No. 5,103,096 issued Apr. 7, 1992 to the present inventor for "Rapid Fire Detector" there were described fire detectors that employ carbon dioxide sensors. In each of those detectors, a fixed threshold is employed, and an alarm signal is generated when the sensed carbon dioxide level, or its rate of change, exceeds the threshold.

If there were absolutely no carbon dioxide present in the atmosphere, detection of fires would be greatly simplified, because any amount of carbon dioxide detected would indicate the present of a fire. However, in reality there is always a small amount of carbon dioxide in the atmosphere, and its concentration ranges from approximately 400 parts per million outdoors to, typically, 1000 parts per million in an office building when people are present.

Thus, depending on where a fire detector is located, the ambient concentration of carbon dioxide may vary with the situation by a factor of three or more. Further, even at a particular location, such as in an office building, the concentration of carbon dioxide may vary in time so that the maximum concentration may be several times the minimum concentration at that location.

These relatively wide variations in the ambient carbon dioxide concentration must be taken into consideration when a threshold is set. In mass-produced fire sensors such as the widely-used domestic smoke detector, the threshold is set at the factory. Due to the above-described variations in the background level of carbon dioxide, it is necessary to set the threshold at a comparatively high level to avoid the occurrence of excessive false alarms. Unfortunately, setting the threshold high renders the instrument less sensitive thereby resulting in a delayed response. A delayed response is very undesirable because of the importance of detecting a fire as early as possible.

Thus it is seen that a fire detector having a fixed threshold is at a disadvantage. Due to the fluctuations in the concentration of carbon dioxide from one location to another and from time to time at any particular location, the threshold must be set relatively high to keep the false alarm rate acceptable, and if this is done, the instrument is necessarily less able to respond quickly to a fire.

SUMMARY OF THE INVENTION

The present invention overcomes the above-described limitation of the fixed-threshold fire sensor by altering the threshold in relation to the existing background concentration of carbon dioxide.

In accordance with the present invention, a microcomputer is provided within the instrument, and it alters the threshold in response to variations in the background concentration of carbon dioxide.

In accordance with the present invention, the threshold remains at a MEDIAL level unless and until the sensed background concentration of carbon dioxide indicates the desirability of increasing the threshold to a single HIGH level or lowering the threshold to a single LOW level.

In accordance with the present invention, a microcomputer derives a number of "derived variables" from the signal that represents the sensed instantaneous concentration of carbon dioxide gas in the air at the sensor. In the preferred embodiment the derived variables are calculated at the end of each successive sampling interval. In the preferred embodiment, the sampling interval is on the order of two to fourteen seconds in duration.

In the preferred embodiment, the derived variables include the average concentration over the sampling interval, the average rate of change of the concentration, the monotonicity of the concentration, and the range of the concentration of carbon dioxide during each interval.

In accordance with the present invention, the decision as to which of the three threshold levels should be used for the next sampling interval is made by reference to a logical combination of the derived variables, as will be described below.

The novel features which are believed to be characteristic of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

Figure 1:
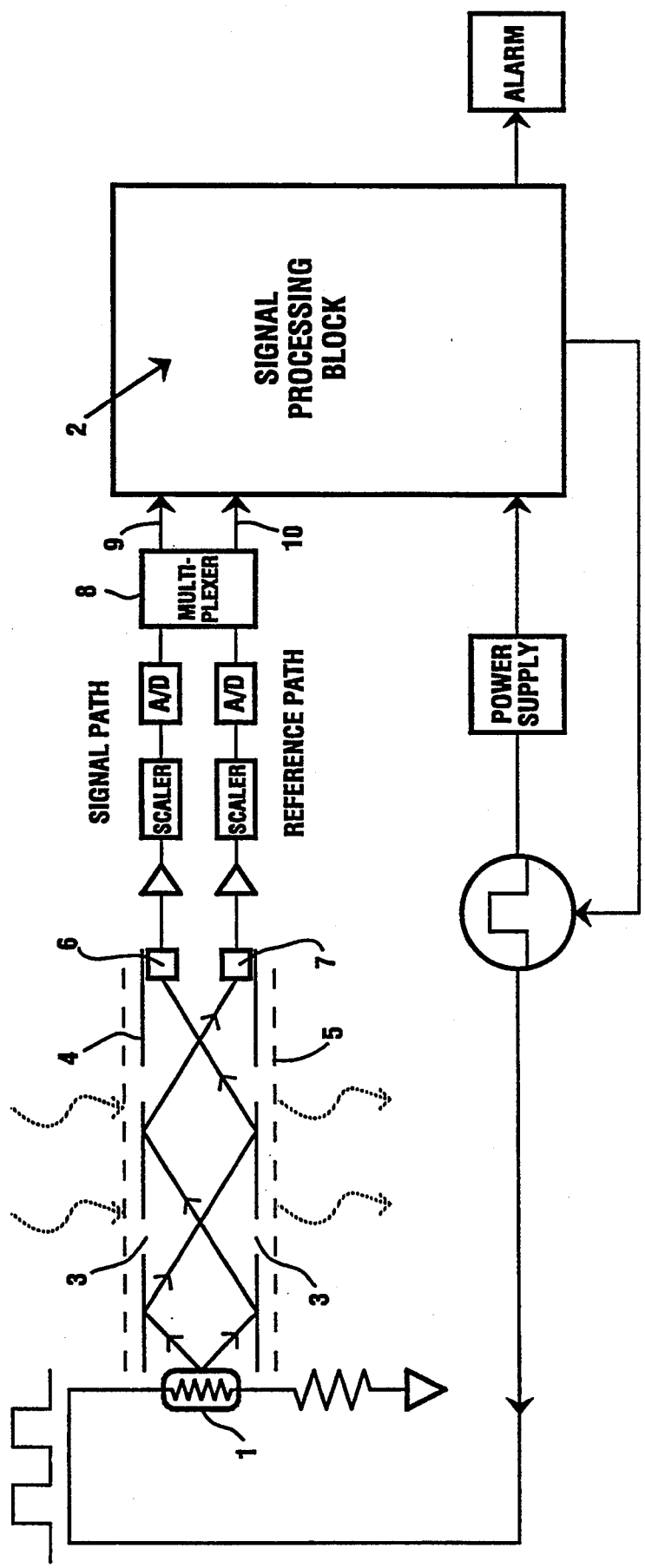
FIG. 1 is a diagram showing the carbon dioxide sensor and the electronic components used in a preferred embodiment of the present invention.

FIG. 1 shows in diagrammatic form the entire adaptive fire detector of the present invention. A miniature incandescent lamp 1 is used as a source of infrared radiation, and in the preferred embodiment it is pulsed at a rate of approximately 1 Hz by a signal processing block 2. The signal processing block is, in essence, a microcomputer which, among other things, generates a square current pulse to energize the incandescent lamp 1.

Infrared radiation produced by the source 1 enters a waveguide structure 4 which acts as a radiation collection element and which also serves as a sample chamber for the carbon dioxide detector. The waveguide structure has a square cross section and has highly reflective inside walls so as to propagate the radiation through it via multiple internal reflections.

The waveguide structure 4 has multiple apertures 3 to permit ambient gases to diffuse easily through the structure 4 in any direction. To protect the inside of the waveguide structure 4 from the degrading effects of dust, smoke, moisture, or harmful oil vapors, the apertures 3 are spanned by a sheet 5 of a semipermeable membrane made of silicone rubber that denies entry to all particles of a size greater than about 0.3 microns.

At the opposite end of the waveguide structure 4 from the, source 1, the propagated radiation is intercepted by two infrared detectors 6 and 7. Detector 6 is equipped with a thin film interference narrow bandpass filter acting as the window of a hermetically sealed canister housing the sensitive detector element and electronic components. The narrow bandpass filter of detector 6 has a wavelength pass band centered at 4.26 microns, coinciding with a strong infrared absorption band of carbon dioxide. The full widths at half-maximum (fwhm) of the filter at detector 6 is about 0.2 microns. The output of detector 6 therefore depends strongly on the concentration of carbon dioxide gas inside the waveguide structure 4. The output of detector 6 will diminish as carbon dioxide diffuses into the waveguide structure.

Detector 7 also has a thin film narrow bandpass filter as its window, having a pass band centered at 3.8 microns, a spectral position devoid of absorptions bands from all commonly encountered gases. Thus the output of detector 7 is relatively unchanged by the presence of any common gases including carbon dioxide inside the waveguide structure 4, and is used as a reference to the output of detector 6. The outputs of detectors 6 and 7 are conditioned before reaching the multiplexer 8 which then sequentially inputs them into the signal processing portion 2. The signal processing portion 2 calculates the ratio of the output of detector 6 to the output of detector 7. The value of this ratio is a function only of the concentration levels of carbon dioxide gas in the waveguide structure 4. Furthermore, the value of the ratio is independent of any physical changes in the source or the sample chamber as a function of time since those changes affect equally the outputs of detectors 6 and 7. The value of the ratio can be calibrated against known concentrations of carbon dioxide gas in the sample chamber to yield what is commonly referred to as the calibration curve of the carbon dioxide sensor.

The operation and structure of this carbon dioxide sensor was described in copending application Ser. No. 07/851,869 filed on Mar. 16, 1992 for "NDIR Gas Analysis Using Spectral Ratioing Technique". The novelty of the present invention resides in combining such a carbon dioxide sensor with the signal processing techniques to be described below which are believed to be novel in their own right.

Of all the gases that are generated at the on-set of a fire, carbon dioxide is the best candidate for detection by a fire detector, as taught in U.S. Pat. Nos. 5,053,754 and 5,103,096 by the present inventor. A carbon dioxide sensor of the type described above can detect carbon dioxide at concentrations on the order of a few parts per million (PPM), making it possible to detect the on-set of a fire at its earliest stages. At those stages, the rate of carbon dioxide gas buildup easily exceeds several tens of PPM per minute.

In reality, other sources of carbon dioxide buildup must be taken into consideration to reduce the likelihood of false alarms. Humans and animals exhale carbon dioxide as part of their metabolic process. The smoking of cigarettes, or cooking on a gas stove or a controlled fire in a fireplace all generate a moderate amount of carbon dioxide. As a result, carbon dioxide may build up at various unknown rates inside a closed room or house. Thus, the setting of a rate threshold for carbon dioxide buildup suffers from the same difficulties as the setting of a threshold on the concentration itself. If the rate is set too low, rate changes caused by extraneous sources will cause an unacceptably high false alarm rate. On the other hand, if the rate threshold is set too high, the ability of the fire detector to detect a slow smoldering fire is compromised.

Figure 2:
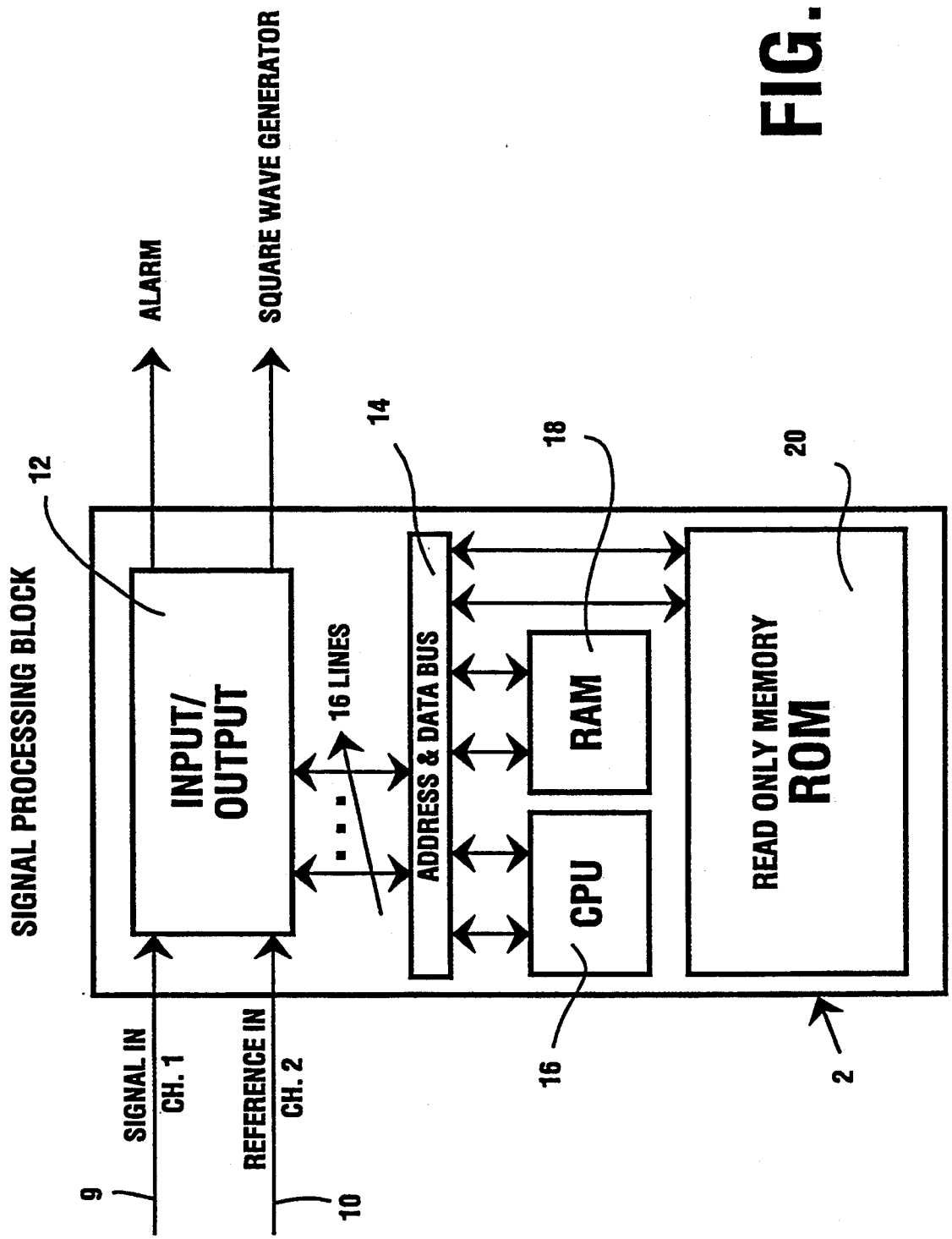
FIG. 2 is a block diagram showing components of the signal processing block of FIG. 1.

As mentioned above, the signal processing portion of the fire detector is a microcomputer in which the signals on the lines 9 and 11) of FIG. 1 are applied, as shown in FIG. 2, to an input/output portion 12 of the microcomputer, in which the bus 14, the central processing unit 16 and the random access memory 18 are used to carry out the necessary calculations under control of instructions stored in the read only memory 20.

Figure 3:
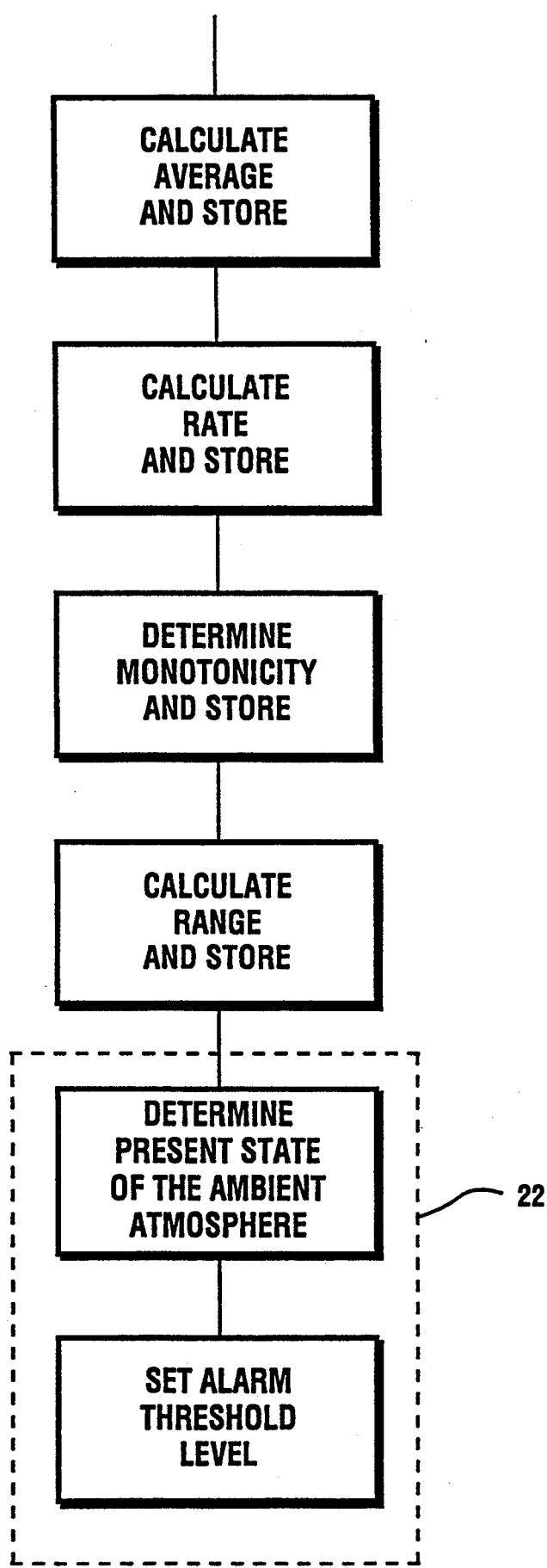
FIG. 3 is a diagram showing the major steps involved in the operation of the signal processing block of FIG. 2.

FIG. 3 shows the calculations preformed by the signal processing microcomputer 2. This calculation program is carried out in the preferred embodiment every ten seconds, although in other embodiments, the sampling interval can be as little as five seconds or as great as 15 seconds.

As shown in FIG. 3, the derived variables include the average value of the concentration of carbon dioxide during the sampling period, the average rate of change of the concentration of carbon dioxide during the sampling period, the monotonicity of the concentration, and the range of the concentration during the sampling interval. By monotonicity is meant whether the increase or decrease of the concentration is always in the same direction, or whether it undergoes at least one reversal of direction during the time interval. Monotonicity is negated by any transition in the sense of the rate, i.e., from positive to negative or from negative to position, that occurs during the sampling interval.

The range is simply the absolute value or magnitude of the difference between the largest value of the concentration and the smallest value of the concentration during a particular sampling interval.

The calculation of the derived variables is performed sequentially rather than in parallel, because speed is not a concern.

Figure 4:
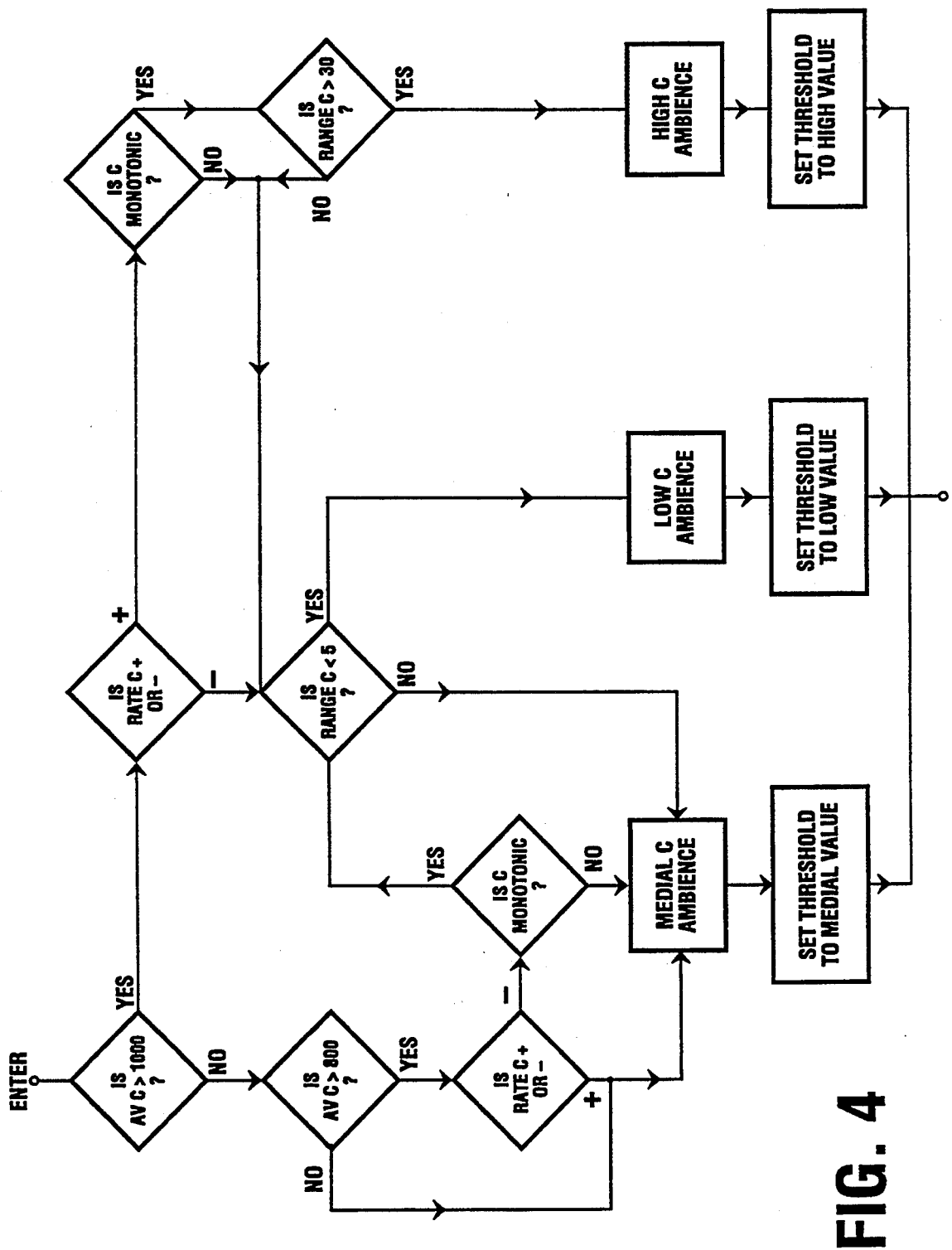
FIG. 4 is a flow chart embodying the logical decision making process for defining the present state of the ambient atmosphere; and, FIG. 5 is a logical truth table corresponding to the flow chart of the FIG. 4 for determining the appropriate threshold level under various conditions.

Once the derived variables have been calculated, the microcomputer 2 uses the derived variables in deciding on an appropriate choice of threshold level. This portion of the calculations is shown in flow chart form in FIG. 4 and in truth table form in FIG. 5.

Thus, in accordance with the present invention the rate threshold for carbon dioxide buildup is determined by the microcomputer 2 according to the condition of the atmosphere at the sensor. In this sense, the fire detector of the present invention is adaptive to its environment.

For a high carbon dioxide ambience, the rate threshold is set high so as to reduce the false alarm rate as much as possible. A typical rate alarm threshold value for high carbon dioxide ambience is around 150 PPM/min. Such a high buildup rate is very rarely encountered except upon the outbreak of an actual fire.

A typical rate alarm threshold for low carbon dioxide ambience may be as low as 5 PPM/min. For such a low carbon dioxide buildup rate, the fire detector has an extremely high speed of response.

For the medial carbon dioxide ambience, the threshold alarm rate is set at 50 PPM/min.

Note that the rate alarm threshold is never permanently set as in other types of fire detectors.

Thus, there has been disclosed a novel alarm rate threshold setting technique which renders the carbon dioxide based fire detector adaptive to its environment and consequently optimized to function at all times as an early fire detector.

The foregoing detailed description is illustrative of one embodiment of the invention, and it is to be understood that additional embodiments thereof will be obvious to those skilled in the art. The embodiments described herein together with those additional embodiments are considered to be within the scope of the invention.

What is claimed is:

1. In a fire detector of the type having a carbon dioxide sensor that produces a concentration signal related to the concentration of carbon dioxide gas in the immediate vicinity of the carbon dioxide sensor, and that applies a rate signal representative of the rate of change of the concentration to a threshold so that an alarm signal is produced when the rate signal exceeds a threshold level, the improvement comprising:
a microcomputer connected to the carbon dioxide sensor and responsive to the concentration signal for producing derived variables for each sampling interval, for continually monitoring the derived variables and for automatically altering the threshold level in relation to the derived variables.

2. The improvement of claim 1 wherein one of the derived variables is the average value of the concentration signal during the sampling interval.

3. The improvement of claim 1 wherein one of the derived variables is the average rate of change of the concentration signal during the sampling interval.

4. The improvement of claim 1 wherein one of the derived variables is the monotonicity of the concentration signal during the sampling interval.

5. The improvement of claim 1 wherein one of the derived variables is the range of the concentration signal during the sampling interval.

6. The improvement of claim 1 wherein said microcomputer determines the threshold level from three possible threshold levels—LOW. MEDIAL, and HIGH—in relation to the derived variables.

7. The improvement of claim 6 wherein the LOW threshold level is approximately 5 PPM/min.

8. The improvement of claim 6 wherein the LOW threshold level is approximately 5 PPM/min, wherein the MEDIAL threshold level is approximately 50 PPM/min., and wherein the HIGH threshold level is approximately 150 PPM/min.

9. In a fire detector of the type having a carbon dioxide sensor that produces a concentration signal related to the concentration of carbon dioxide gas in the immediate vicinity of the carbon dioxide sensor, and that applies a rate signal representative of the rate of change of the concentration to a threshold so that an alarm signal is produced when the rate signal exceeds a threshold level, the improvement comprising:
a microcomputer connected to the carbon dioxide sensor and responsive to the concentration signal for producing derived variables for each sampling interval, for continually monitoring the derived variables and for automatically altering the threshold level in relation to the derived variables, wherein the derived variables include the average value of the concentration signal during the sampling interval, the average rate of change of the concentration signal during the sampling interval, the monotonicity of the concentration signal during the sampling interval, and the range of the concentration signal during the sampling interval.

10. The improvement of claim 1 wherein said microcomputer determines the threshold level from the values of the derived variables in accordance with the following table:

| DERVIED VARIABLES | | | | | | |
|---|---|---|---|---|---|---|
| AVERAGE | | RATE $1=+$ | MONO $1=$ YES | RANGE | | TRESHOLD |
| <800 | >1000 | $0=-$ | $0=$ NO | <5 | >30 | LEVEL |
| 0 | 1 | 1 | 1 | 0 | 1 | HIGH |
| 0 | 0 | | | | | MEDIAL |
| 1 | 0 | 1 | | | | |
| 1 | 0 | 0 | 0 | | | |
| 1 | 0 | 0 | 1 | 0 | | |
| 0 | 1 | 0 | | 0 | | |
| 1 | 0 | 0 | 1 | 1 | 0 | LOW |
| 0 | 1 | 0 | | 1 | 0 | |
| 0 | 1 | 1 | 0 | 1 | | |
| 0 | 1 | 1 | 1 | 1 | 0 | | where:
AVERAGE is the average value of the concentration of carbon dioxide during the sampling period "1" denotes "yes" and "0" denotes "no"),
RATE is the average rate of change of the concentration of carbon dioxide during the sampling period "1" denotes an increasing concentration and "0" denotes a decreasing concentration),
MONO refers to whether the increase or decrease of the concentration is monotonic during the sampling period "1" denotes "yes" and "0" denotes "no"); and,
RANGE is the magnitude of the difference between the largest and smallest values of the concentration during the sampling period ("1" denotes "yes" and "0" denotes "no").

* * * * *